(12) United States Patent
Porter et al.

(10) Patent No.: US 7,794,431 B2
(45) Date of Patent: Sep. 14, 2010

(54) APPARATUS AND METHOD FOR FACILITATING THE REPLACEMENT OF AN IMPLANTED CATHETER

(75) Inventors: Christopher H. Porter, Woodinville, WA (US); Claude A. Vidal, Santa Barbara, CA (US); Russ J. Redmond, Goleta, CA (US); Byron L. Moran, Santa Barbara, CA (US); Paul Kaluzniak, Simi Valley, CA (US); Abram D. Janis, Valencia, CA (US)

(73) Assignee: Incumed LLC, Valencia, CA (US)

( * ) Notice: Subject to any disclaimer, the term of this patent is extended or adjusted under 35 U.S.C. 154(b) by 351 days.

(21) Appl. No.: 11/650,795

(22) Filed: Jan. 6, 2007

(65) Prior Publication Data
US 2007/0112334 A1 May 17, 2007

Related U.S. Application Data

(63) Continuation-in-part of application No. 10/821,383, filed on Apr. 9, 2004, now Pat. No. 7,604,617.

(60) Provisional application No. 60/462,265, filed on Apr. 12, 2003.

(51) Int. Cl.
*A61M 5/00* (2006.01)
(52) U.S. Cl. .......................... 604/175; 604/171; 604/11
(58) Field of Classification Search ................ 604/175, 604/533–539, 890.1, 891.1, 892.1, 164.04, 604/164.07, 165.01, 174, 178, 240–243; 206/438–440, 63.3, 63.5
See application file for complete search history.

(56) References Cited

U.S. PATENT DOCUMENTS 3,447,164 A 6/1969 Weikel
(Continued)

FOREIGN PATENT DOCUMENTS

EP 0 367 354 B1 2/1993

OTHER PUBLICATIONS

Jensen, J.A. Tissue reaction to soft-tissue anchored percutaneous implants in rabbits Journal of Biomedical Medical Research, 1994 vol. 28, pp. 1047-1054.

(Continued)

*Primary Examiner*—Nicholas D Lucchesi
*Assistant Examiner*—Leah Stohr
(74) *Attorney, Agent, or Firm*—Freilich, Hornbaker & Rosen

(57) ABSTRACT

A medical apparatus and method of use for implanting a percutaneous catheter in a patient's body which catheter can be easily positioned, repositioned, and replaced. The apparatus includes an elongate sleeve comprising a wall surrounding an interior elongate passageway. The passageway extends from a sleeve proximal end to a sleeve distal end. The sleeve is intended to be percutaneously implanted through an incision in the patient's skin so that the sleeve distal end resides subcutaneously. The sleeve outer peripheral surface carries a layer of porous material intended to be placed just under the patient's outer skin layer in contact with the dermis to promote tissue ingrowth for anchoring the sleeve and forming an infection resistant barrier. The sleeve passageway is dimensioned to snugly accommodate the outer surface of catheter while permitting the catheter to slide relative to the sleeve. A sealing device is mounted around the catheter adjacent to the sleeve proximal end to prevent deleterious material from migrating into the patient's body along the catheter outer surface.

20 Claims, 6 Drawing Sheets

U.S. PATENT DOCUMENTS

| | | | |
|---|---|---|---|
| 3,783,868 A | | 1/1974 | Bokros |
| 4,278,092 A | | 7/1981 | Borsanyi et al. |
| 4,379,506 A | * | 4/1983 | Davidson .................... 206/364 |
| 4,417,888 A | | 11/1983 | Cosentino et al. |
| 4,488,877 A | | 12/1984 | Klein et al. |
| 4,496,349 A | | 1/1985 | Cosentino |
| 4,648,391 A | | 3/1987 | Ellis |
| 4,668,222 A | * | 5/1987 | Poirier ....................... 604/175 |
| 4,728,331 A | | 3/1988 | Russier |
| 4,729,366 A | | 3/1988 | Schaefer |
| 4,781,693 A | | 11/1988 | Martinez et al. |
| 4,781,694 A | | 11/1988 | Branemark et al. |
| 4,886,502 A | | 12/1989 | Poirier et al. |
| 5,059,186 A | * | 10/1991 | Yamamoto et al. .......... 604/537 |
| 5,085,646 A | | 2/1992 | Svenson et al. |
| 5,098,434 A | | 3/1992 | Serbousek |
| 5,152,298 A | * | 10/1992 | Kreyenhagen et al. ...... 607/116 |
| 5,407,354 A | * | 4/1995 | Fife ........................... 433/116 |
| 5,411,467 A | | 5/1995 | Hortmann et al. |
| 5,569,295 A | * | 10/1996 | Lam ........................... 606/198 |
| 5,931,838 A | | 8/1999 | Vito |
| 6,099,508 A | | 8/2000 | Bousquet |
| 6,544,206 B1 | * | 4/2003 | Johnston, Jr. .............. 604/4.01 |
| 6,955,677 B2 | | 10/2005 | Dahneers |
| 2004/0111138 A1 | * | 6/2004 | Bleam et al. ................ 607/105 |
| 2004/0204686 A1 | | 10/2004 | Porter et al. |
| 2005/0251102 A1 | * | 11/2005 | Hegland et al. ............. 604/500 |

OTHER PUBLICATIONS

Bandyopadhyay, Balaji et al., A "traffic control" role for TGFb3: orchestrating dermal and epidermal cell motility during wound healing Journal of Cell Biology, Mar. 27, 2006 vol. 172, No. 7, pp. 1093-1105.

* cited by examiner

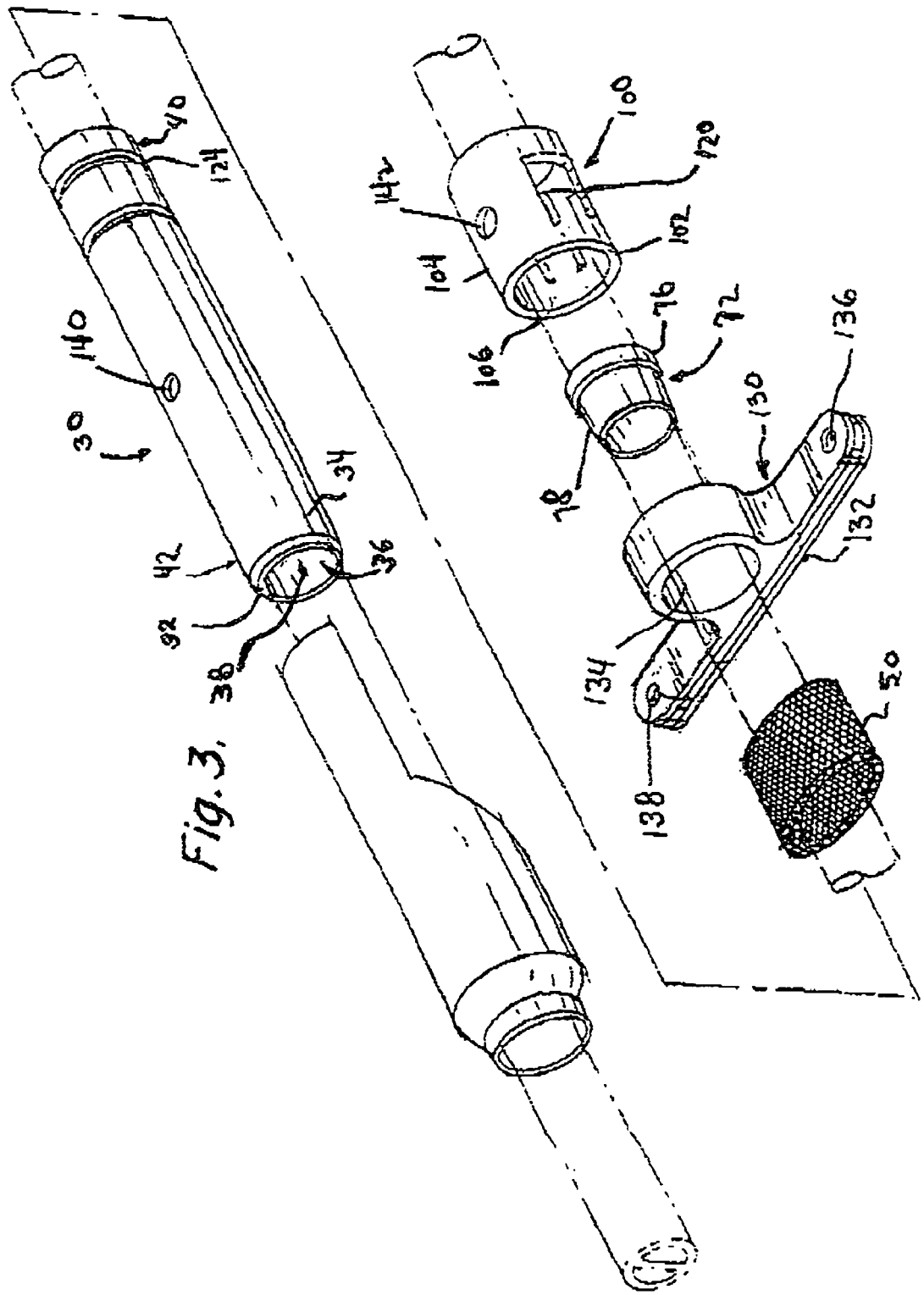

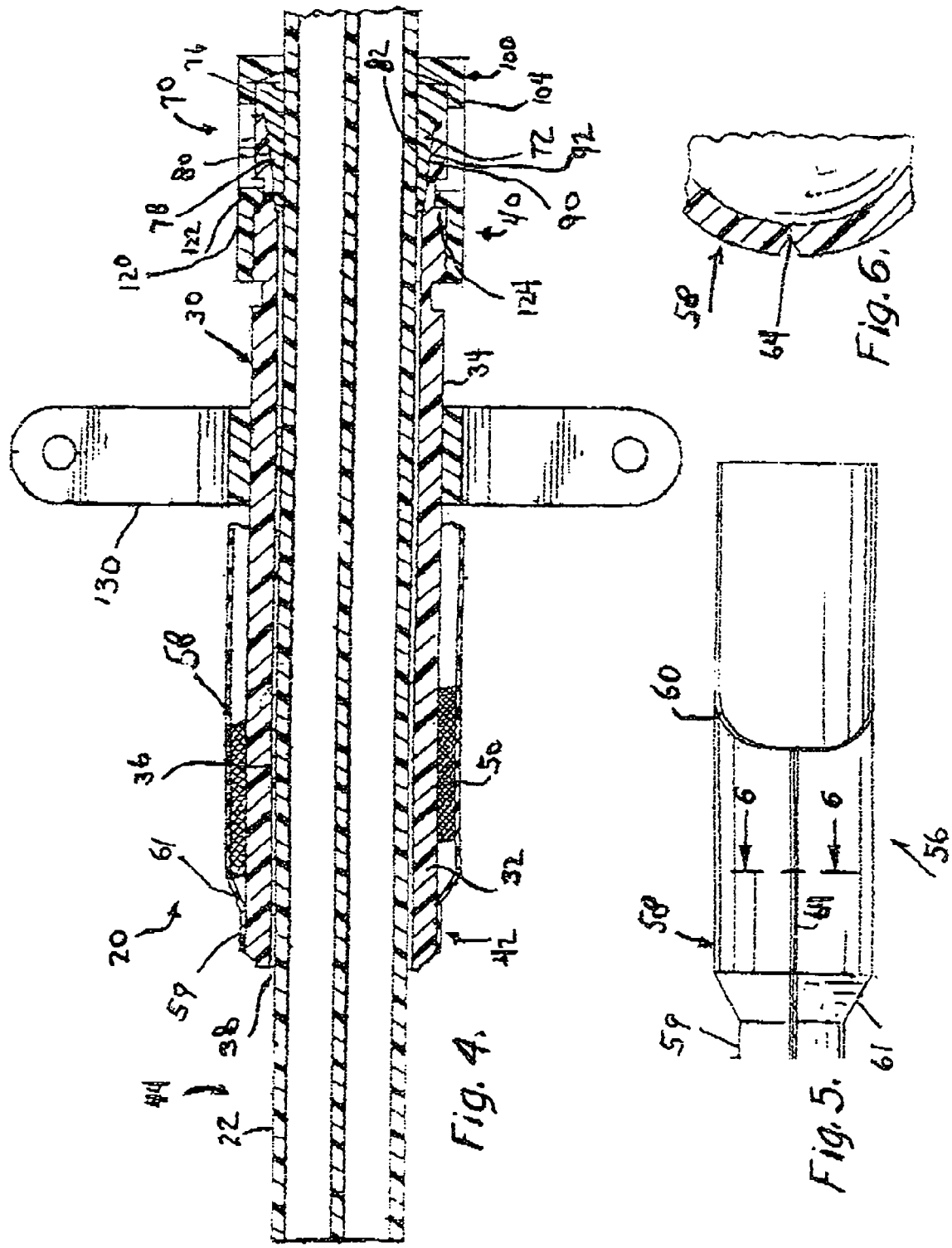

APPARATUS AND METHOD FOR FACILITATING THE REPLACEMENT OF AN IMPLANTED CATHETER

RELATED APPLICATIONS

This application is a Continuation-In-Part of U.S. application Ser. No. 10/821,383 filed on Apr. 9, 2004 now U.S. Pat. No. 7,604,617 which claims priority based on U.S. Provisional Application Ser. No. 60/462,265 filed on Apr. 12, 2003. This application claims priority based on the aforementioned applications, whose disclosures are, by reference, incorporated herein and on U.S. Provisional Application Ser. No. 60/758,137 filed on Jan. 11, 2006.

FIELD OF THE INVENTION

This invention relates generally to medical technology and more particularly to a method and apparatus for implanting an elongate conduit, e.g., a catheter or cable, so as to extend through a patient's skin for providing long term access to an interior body site. Embodiments of the invention are useful in a variety of applications, e.g., in hemodialysis procedures to provide access to the patient's central venous system.

BACKGROUND OF THE INVENTION

In a variety of medical procedures, catheters are implanted through a patient's skin to provide long term access to interior body sites; e.g., blood vessels and organs. Unless adequate precautions are taken, infections and inflammation are likely to occur around the site where the catheter penetrates the skin. To mitigate such problems, a tissue integrating cuff is sometimes attached to the catheter and placed under the patient's skin to resist infection. Although such a cuff can reduce the likelihood of infection, its presence increases the difficulty of removing and/or repositioning the implanted catheter. More particularly, it is not uncommon for an implanted catheter to become damaged, e.g., clogged or kinked, over an extended period of use thus necessitating catheter removal and/or replacement. When this occurs, the cuff must be dissected thereby complicating and prolonging the surgical procedure.

The aforementioned application Ser. No. 10/821,383 describes the use of a tissue integrating structure on a percutaneously implanted medical device for anchoring the device and creating an infection resistant barrier around the device.

SUMMARY OF THE INVENTION

The present invention is directed to a medical apparatus and method of use for percutaneously implanting an elongate conduit, e.g., a catheter or cable, in a patient's body in a manner which allows the conduit to be easily positioned, repositioned, and replaced.

An apparatus in accordance with the invention includes an elongate sleeve comprising a wall surrounding an interior elongate passageway. The passageway extends from a sleeve proximal end to a sleeve distal end. The sleeve is intended to be percutaneously implanted through an incision in the patient's skin so that the sleeve distal end resides beneath the skin, i.e., subcutaneously, and the sleeve proximal end resides above the skin. The sleeve outer peripheral surface carries a layer of porous material, e.g., a biocompatible mesh, as described in U.S. application Ser. No. 10/821,383, intended to be placed just under the patient's outer skin layer in contact with the dermis to promote tissue ingrowth for anchoring the sleeve and forming an infection resistant barrier. The sleeve passageway is dimensioned to snugly accommodate the outer surface of a conduit (which will hereinafter be assumed to be a catheter unless otherwise stated) while permitting the catheter to slide in the passageway relative to the sleeve. A sealing device extends around the catheter near the sleeve proximal end to prevent deleterious material from migrating into the patient's body along the catheter outer surface.

In accordance with one preferred embodiment, the sealing device includes a compressible annular seal which cooperates with the sleeve proximal end to close a potential migration path along the catheter outer surface. Preferably, the sleeve wall inner surface at its proximal end tapers outwardly to form a wedge recess for accommodating at least a portion of the annular seal. A locking, or compression, member is mounted around the catheter for longitudinal movement along the catheter to compress the seal in the recess between the sleeve wall and catheter outer surface. Latching means are provided for latching the compression member to the sleeve to maintain adequate compression between the seal, the sleeve wall, and the catheter outer surface.

In typical use, a physician will make an incision proximate to the patient's chest or abdomen. A surgical tunneler tool is then typically inserted through the incision to form a subcutaneous tunnel to an interior site through which a catheter can be inserted. In accordance with a preferred embodiment, a sleeve, an annular seal, and a compression member, are mounted on the catheter as previously described. The distal end of the sleeve is then inserted through the incision to locate the sleeve porous layer in contact with the dermis just below the patient's outer skin surface. The sleeve proximal end is then preferably anchored adjacent to the patient's exterior skin surface. With the sleeve anchored and the compression member in its unlocked state, the physician is able to slide and/or rotate the catheter within the sleeve for optimum catheter positioning. When the catheter is properly positioned, the annular seal is moved along the catheter against the sleeve proximal end to engage a portion in the wedge recess. The compression member can then be brought up against and latched to the sleeve thus compressing the seal therebetween and preventing relative movement between the catheter and sleeve. With the sleeve thus implanted, the patient's subcutaneous tissue will, over time, grow into the porous material to anchor the sleeve and form an infection resistant barrier. The porous material may be coated or impregnated with constituents having antimicrobial and/or anti-inflammatory properties to promote healing, e.g., silver containing compounds or antibiotic eluting coatings and/or steroids.

In one preferred embodiment of the invention, the porous layer on the sleeve is covered prior to use by a protective sheath of thin flexible material. The sheath prevents abrasion damage as the sleeve porous layer is inserted through the incision. The sheath is preferably configured with a projecting tab which allows the physician to readily peel the sheath away, e.g., along a preformed score line, as the sleeve is inserted through the incision to place the porous layer adjacent the patients dermis.

After the sleeve and catheter have been implanted, subcutaneous tissue will gradually grow into the porous layer to form an infection resistant barrier around the sleeve to prevent fluid and/or other deleterious material from migrating into the body along the sleeve outer surface. The annular seal functions to prevent deleterious material from migrating along the catheter outer surface. An apparatus in accordance with the invention enables the physician at some later date (e.g., months) to replace the implanted catheter while leaving the sleeve in place. To do this, the physician will first unlatch the existing compression member to allow the old catheter to be withdrawn from the sleeve proximal end. A new catheter, preferably carrying a new seal and compression member, is then inserted through the sleeve. The new compression member is then latched to the existing sleeve to compress the annular seal therebetween to seal the path along the catheter outer surface.

As was previously mentioned, once the sleeve has been anchored, if the compression member is unlatched, the physician can slide and/or rotate the catheter relative to the sleeve for optimum catheter positioning, prior to latching the compression member to hold the catheter in place. In order to prevent the introduction of deleterious material into the body when the catheter is being inwardly adjusted, it is preferable to form a sterile field around that portion of the catheter which can move inwardly past the annular seal. Thus, in a preferred embodiment, an extensible seal member, e.g., a bellows like sheath, is mounted around the catheter with the distal end of the bellows sheath sealed to the compression member and the proximal end of the bellows sheath sealed to the catheter outer surface. This arrangement maintains the portion of the catheter distal from the bellows proximal end within a sterile field to avoid introducing deleterious material past the annular seal when the catheter is adjusted inwardly.

BRIEF DESCRIPTION OF THE FIGURES

FIG. 3 is an exploded view of the assembly of FIG. 2 showing a catheter in phantom together with a protective sheath, a sleeve, a layer of porous material, a sleeve anchor, an annular seal, and a compression member;

FIG. 4 is a sectional view taken substantially along the plan 44 of FIG. 2;

FIG. 5 is a plan view of the protective sheath;

FIG. 6 is a sectional view taken substantially along the plan 6-6 of FIG. 5 particularly showing a performed score line;

DETAILED DESCRIPTION

Various medical regimens utilize a percutaneously implanted flexible elongate conduit to provide access to an interior body site. For example, hemodialysis drug infusion, plasmapheresis, and other procedures typically employ a percutaneously implanted catheter for delivering fluid to or extracting fluid from an interior body site. Other procedures utilize an electric cable to deliver an electric signal to, or extract an electric signal from, an interior body site. The present invention is directed to a method and apparatus for facilitating the long term implantation and utilization of a flexible elongate conduit and for facilitating the positioning, repositioning, and replacement, or exchange, of the conduit.

Figure 1:
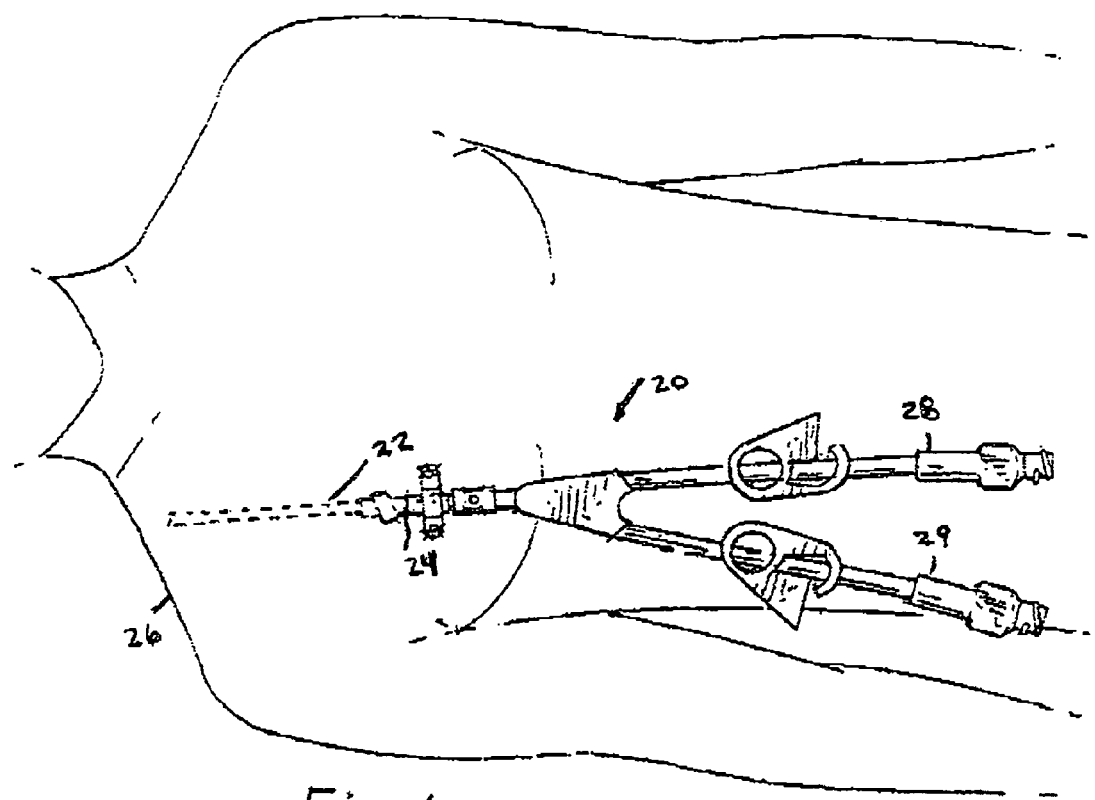
FIG. 1 is a schematic representation depicting a medical device in accordance with the invention for percutaneously implanting a catheter for an exemplary hemodialysis application.

FIG. 1 schematically depicts an apparatus 20 in accordance with the invention for percutaneously implanting a catheter 22 through an incision 24 in a patient 26 undergoing an exemplary hemodialysis procedure. In such a procedure, a dual lumen catheter 22 is typically used with the two lumen respectively coupled to separate exterior flow couplers 28 and 29.

Figure 2:
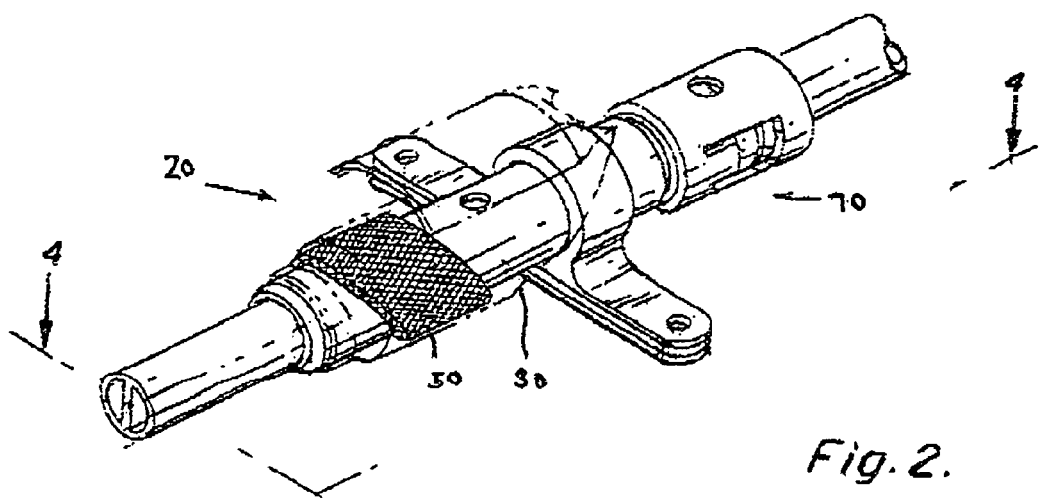
FIG. 2 is an isometric view of a preferred catheter assembly in accordance with the invention.

Attention is now directed to FIGS. 2-4 which depict a preferred catheter assembly 20 in accordance with the present invention. The assembly 20 is comprised of an elongate sleeve 30 formed by a sleeve wall 32 having a peripheral outer surface 34 and a peripheral inner surface 36. The inner surface 36 surrounds a passageway 38 extending from a first, or proximal, end 40 to a second, or distal, end 42.

The sleeve 30 is shown mounted on a catheter 22 extending through the passageway 38. The catheter outer surface 44 and passageway wall surface 36 are closely dimensioned but with sufficient clearance therebetween to enable the catheter to slide axially in the passageway.

Figure 12:
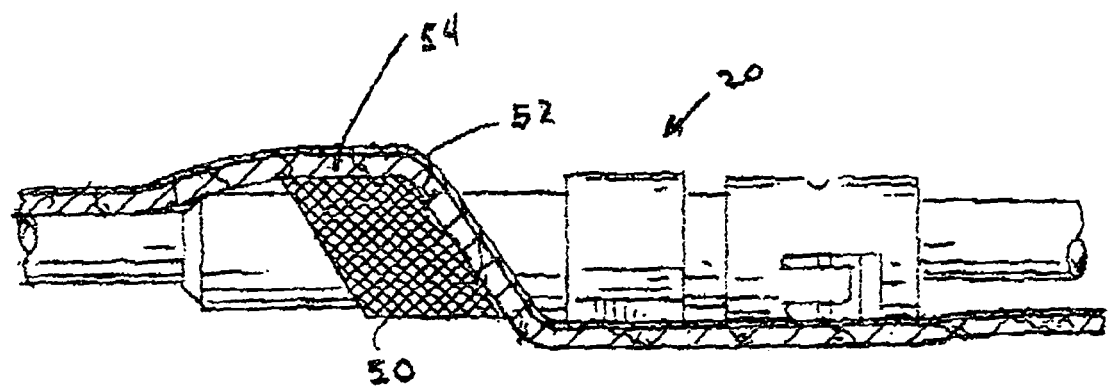
FIG. 12 shows a cross-sectional view of the catheter assembly as implanted with the porous layer adjacent the patient's dermis.

A layer 50 of porous material, e.g., titanium mesh, as described in said U.S. application Ser. No. 10/821,383, is mounted on the sleeve 30 close to the sleeve distal end 42. In use, it is intended that the sleeve distal end be inserted through an incision in the patient's skin to position the porous layer 50 just below the patients epidermis skin layer 52 and adjacent to the patient's dermis layer 54 (FIG. 12) in contact with the patient's dermis layer 54. Note that the porous layer 50 is preferably oriented diagonally with respect to the axis of sleeve 30 to better conform to the patient's skin contour (FIG. 12). This orientation optimizes contact between the porous layer 50 and the patient's dermis to promote, over time soft tissue ingrowth into the porous layer. This tissue ingrowth acts to form an infection resistant barrier around sleeve 30. This barrier may be enhanced by incorporating antimicrobial and/or anti-inflammatory constituents into the porous layer 50. For example, silver containing compounds and/or antibiotic eluting coatings can be used as antimicrobial agents and steroids can be used as anti-inflammatory agents.

A protective sheath 56 (FIGS. 4-6) is preferably mounted around sleeve 30 and porous layer 50 prior to use to avoid tissue abrasion damage when the sleeve distal end 42 is inserted through the patient's incision. The protective sheath 56 is preferably formed of thin flexible tubular material (e.g., 0.010 wall FEP tubing). As will be further discussed hereinafter, the sheath 56 is removed from the sleeve 30 by the physician after the sleeve and porous layer have been inserted through the incision.

More particularly, the sheath 56 is preferably configured as a substantially tubular, e.g., cylindrical, body 58 having a distal collar 59 and a proximal elongate pull tab 60. An outwardly tapering section 61 extends from the collar 59 to the main body portion 58. Note that the collar 59 and distal portion of section 61 have a diameter smaller than that of the porous layer 50. For example only, the sleeve 30 may have an outer diameter of 0.250 inches, the porous layer 50 an outer diameter of 0.310 inches and the collar 59 an inner diameter of 0.193 inches. An axially oriented score, or perforated line 64 is preformed through the collar 59, the tapering section 61 and the body portion 58 to facilitate the physician peeling the sheath 56 from the sleeve 30. Note in FIG. 4 that the sheath fits tightly around the periphery of sleeve 30 and porous layer 50 and that the tapering section 61 is positioned distally of the porous layer 50. In use, the physician is able to readily peel the sheath from the sleeve with one hand by rolling, or winding, the elongate tab 60 to pull the sheath axially in a proximal direction. Peeling occurs because the sheath is pulled proximally, the tapering section 61 and collar 59 have to move past the larger diameter porous layer 50 which action causes the sheath to tear along score line 64 allowing it to be easily stripped from the sleeve 30.

As has previously been mentioned, in use, dermis tissue grows into the porous layer 50 to form a barrier preventing deleterious material from migrating into the patient's body along the sleeve outer surface 34. In order to prevent migration of deleterious material into the body along the narrow gap between the catheter outer surface 44 and the sleeve inner surface 36, a sealing device 70 is provided. A preferred sealing device 70 is comprised of a seal member 72, preferably in the form of a compressible annular member or ring. The seal member 72, as shown in FIGS. 3 and 4, includes an end flange 76 having a distally extending body portion 78. The outer surface 80 of body portion 78 is preferably conically shaped narrowing in a direction distal from the end flange 76. The seal member 72 has an inner peripheral surface 82 surrounding an interior bore for accommodating the catheter 22. With the seal member 72 in its quiescent uncompressed state, the inner surface 82 is sufficiently large to allow the member 72 to slide along the catheter outer surface 44.

The inner surface 36 of sleeve 30 tapers outwardly at 90 adjacent to the sleeve proximal end 40. The outward tapering of the surface 36 forms a wedge recess 92 for receiving the body portion 78 of the seal member 72 (FIG. 4).

The sealing device 70 further includes a locking, or compression, member 100 comprising a tubular wall 102 having an outer peripheral surface 104 and an inner peripheral surface 106 surrounding a bore for accommodating the catheter 22. The compression member 100 is configured so that in its unlocked state, it can slide distally along catheter 22 into latching engagement (locked state) with the sleeve 30 while compressing the annular seal member 72 into the wedge recess 92. When so compressed, the seal member 72 seals against the catheter outer surface 44 and the sleeve inner surface 90 to prevent migration of deleterious material into the patient's body. Moreover, when the seal member 72 is compressed by the latched compression member 100, it locks the catheter to the sleeve to prevent relative movement therebetween.

For the purpose of latching to the sleeve, the compression member 100 is provided with one or more cantilevered resilient fingers 120. Each finger has a terminal projection 122 configured to snap into a groove 124 (FIG. 4) formed in the sleeve outer surface 34 proximate to the sleeve proximal end 40. So, during the installation of the catheter assembly 20, the physician can slide the compression member 100 distally along catheter 22 toward the sleeve 30 to compress the seal member 72 therebetween until the projection 122 latches into groove 124. With the seal member 72 thus compressed, it acts to frictionally lock the catheter 22 to the sleeve 30.

The compression member 100 can be unlatched by pulling the resilient finger 120 radially outward withdraw to the projection 122 from the groove 124. This allows the compression member 100 to be moved proximally along the catheter thus decompressing the seal member 72 and permitting the physician to reposition the catheter or remove the catheter through the sleeve 30 to exchange it with a replacement catheter.

An anchor 130 is provided for anchoring the sleeve proximal end 40 to the patient's skin. The anchor 130 is comprised of a base 132 supporting a catheter guide 134. The guide 134 defines a bore for accommodating the sleeve 30. The base is preferably provided with holes 136, 138 for suturing the anchor 130 to the patient's skin.

FIGS. 7-12 schematically depict successive steps in an exemplary procedure for implanting the catheter assembly 20 shown in FIGS. 1-6.

Figure 7:
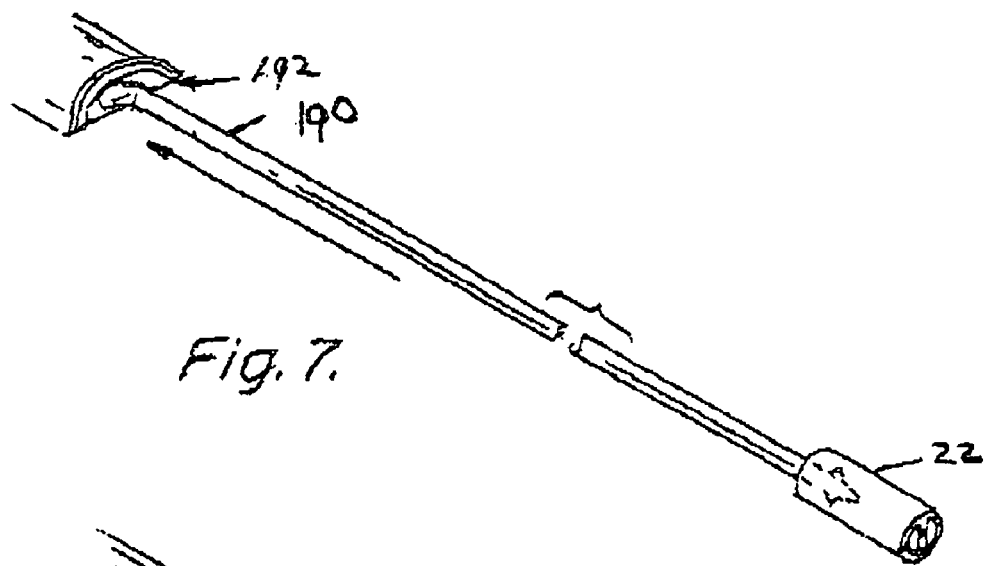
FIGS. 7-11 show successive steps in an exemplary procedure for implanting and utilizing the catheter assembly in accordance with the invention.

FIG. 7 shows the use of a conventional tunneler tool 190 being inserted through a patient's incision 192 to form a tunnel through which the distal end of the catheter 22 is pulled by the proximal end of tool 190.

Figure 8:
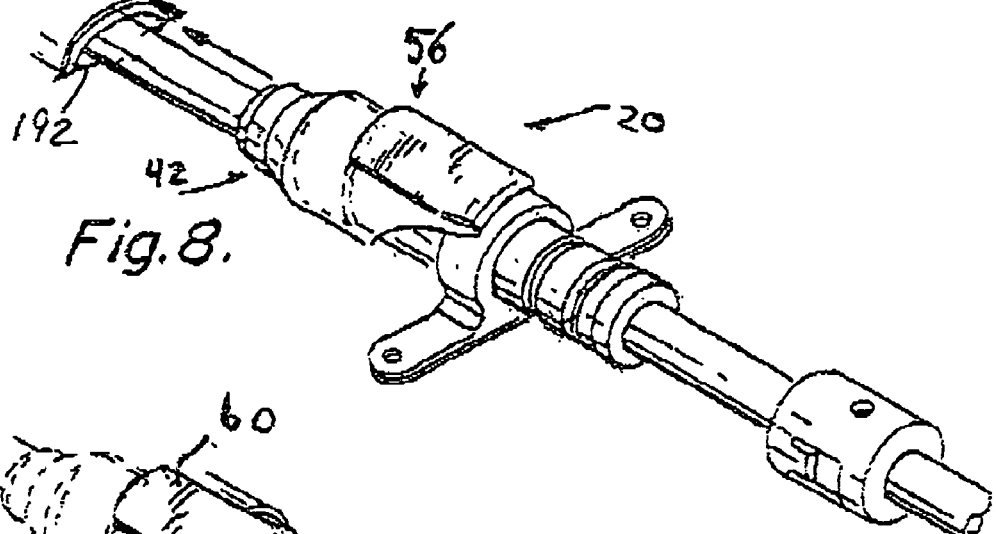

FIG. 8 shows the catheter assembly 20 with the sleeve distal end 42 and protective sheath 60 being inserted through the incision 192.

Figure 9:
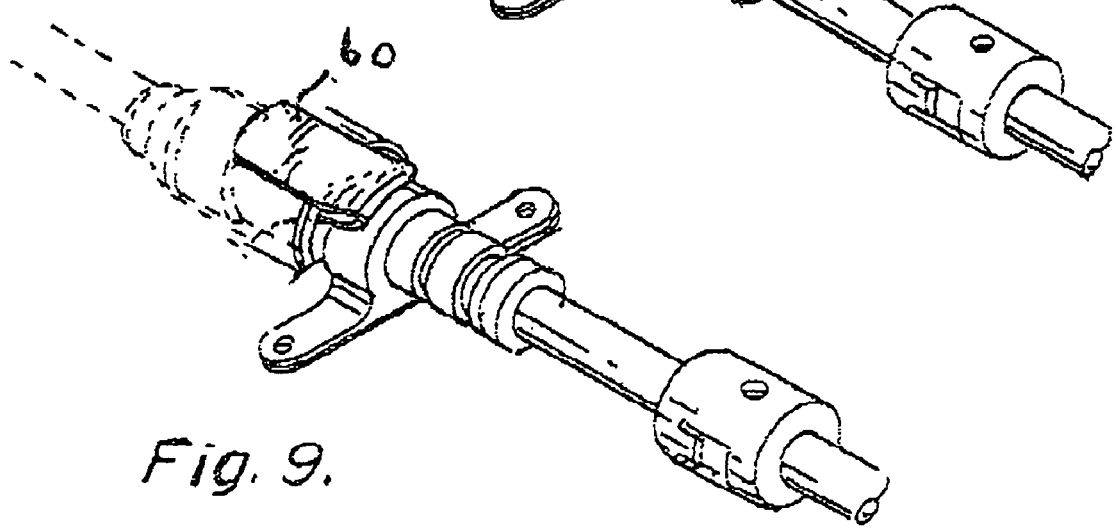

FIG. 9 shows the catheter assembly 20 inserted further into the incision for positioning the porous layer 50 just beneath the epidermal skin layer 52 and adjacent to the dermis layer 54 (FIG. 12). Note the protective sheath tab 62 extending outwardly from the sleeve.

Figure 10:
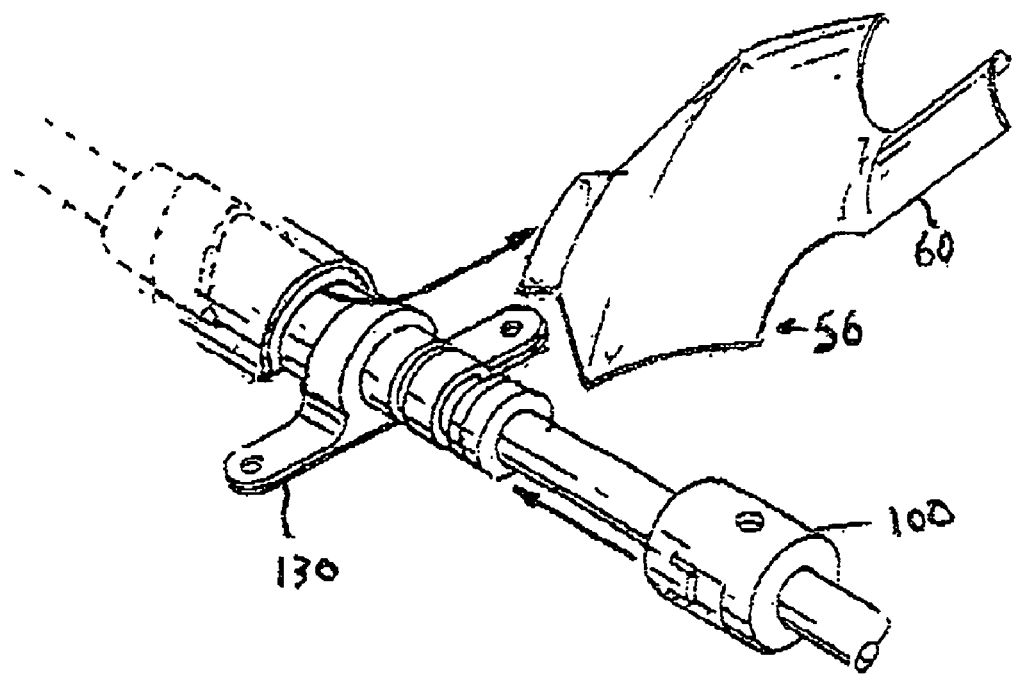

FIG. 10 shows the protective sheath 56 being peeled away (as a consequence of the physician pulling tab 60) from the sleeve 30 to directly expose the porous layer 50 to the patient's dermis.

Figure 11:
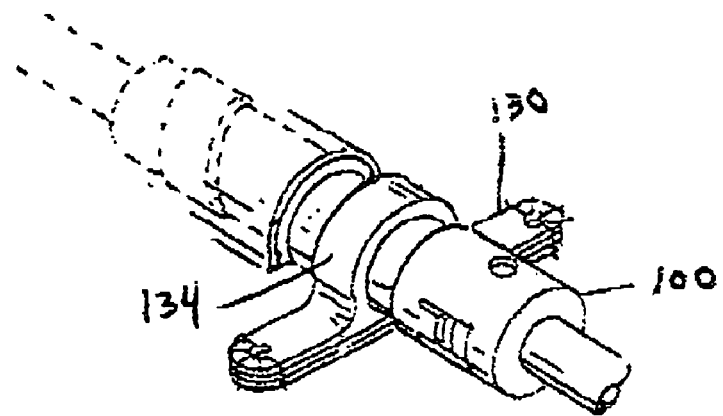

FIG. 11 shows the anchor 130 sutured to the patient's skin to thus securely hold the sleeve proximal end 40 and facilitate the latching of compression member 100 to sleeve 30. In order to latch the compression member, the physician should first align the index marks 140 on sleeve 30 and 142 on compression member 100 (FIGS. 3-4) prior to sliding member 100 against sleeve 30 to latch projection 122 into groove 124.

FIG. 12 shows a cross-section of the installed catheter assembly 20 with the porous layer 50 contacting the patient's dermis 54 to promote tissue ingrowth.

Figure 13:
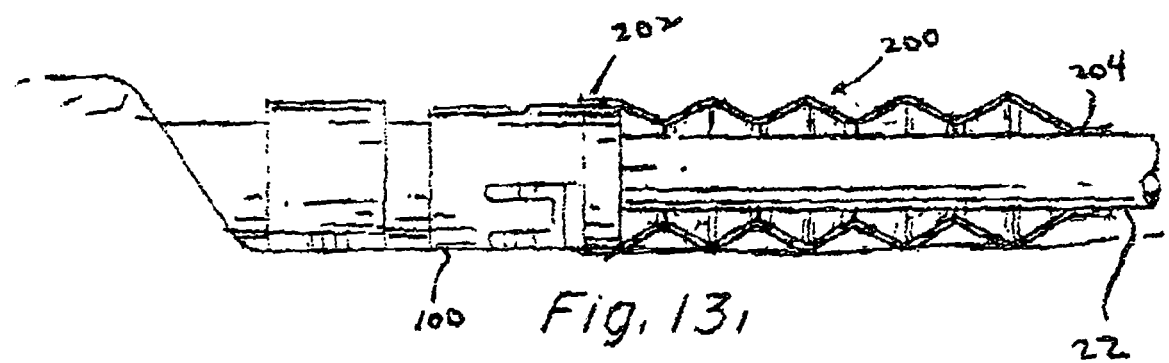
FIG. 13 shows an optional extensible seal member which can be used to create a sterile field around the catheter adjacent to the sleeve proximal end to enable the catheter to be inwardly adjusted while preventing the introduction of deleterious material along the path between the catheter outer surface and the sleeve inner surface.

After initial implantation of the catheter 22 as depicted in FIGS. 7-12, it is sometimes desirable to reposition the catheter for more effective treatment and/or to reduce patient discomfort. Such repositioning can involve slightly adjusting the position and/or orientation of the catheter distal end and is achieved by unlatching the compression member 100 and then sliding the catheter into or out of the sleeve and/or by rotating the catheter. In order to avoid introducing deleterious material when the catheter is pushed distally, it is desirable to create a sterile field around that portion of the catheter which can move distally past the annular seal member 72. As shown in FIG. 13, an extensible seal member 200, e.g., a bellows, is provided. The seal member 200 has a distal end 202 which is sealed to the compression member 100 and a proximal end 204 which is sealed to the catheter 22.

It is further pointed out that with the compression member 100 unlatched, an implanted catheter can be fully withdrawn through the sleeve for replacement by a new catheter. Although different technique can be employed, it is contemplated that the physician will thread a guide wire through the old catheter prior to withdrawing it. The new catheter is then threaded along the guide wire and through the sleeve. When the new catheter is properly placed, the guide wire is withdrawn. The new catheter preferably carries a new seal member 72 and compression member 100.

From the foregoing, it should now be understood that a method and apparatus has been described for positioning, repositioning, and/or replacing an elongate conduit extending through a patient's skin. In use, the physician will manipulate the conduit portion extending exteriorly of the patient's skin to position and orient the conduit distal end adjacent to a selected interior body site. When the distal end is properly positioned, the compression member is latched to thereby lock the conduit relative to the implanted sleeve. As previously noted, the conduit can comprise a catheter for delivering an/or extracting fluid to/from the interior body site or an electric cable for delivering and/or deriving an electric signal to/from the interior body site. In some situations, it may be desirable to use both a catheter and an electric cable. Although only a limited number of structural embodiments have been described, it is recognized that various modifications and alterations will occur to persons skilled in the art which fall within the spirit and intended scope of the invention as defined by the appended claims.

The invention claimed is:

1. An assembly useful for providing medical access to internal body sites, said assembly comprising:

an elongate sleeve having a distal end configured for insertion through a patient's skin incision for accommodating an elongate conduit;

said sleeve comprising a peripheral wall having an outer surface including a distal portion extending axially from said sleeve distal end toward a sleeve proximal end, said sleeve outer surface distal portion having a substantially uniform diameter dimensioned to be inserted through said incision;

said sleeve peripheral wall having an inner surface surrounding an axial passageway extending from said distal end to said proximal end;

a layer of porous material surrounding said distal portion dimensioned to be inserted through said incision for subcutaneous placement in contact with a patient's dermis layer to promote tissue in-growth and form an infection resistant barrier;

an elongate conduit comprising a peripheral wall having an outer surface extending from a proximal end to a distal end;

said sleeve inner surface and said conduit outer surface being dimensioned to allow said conduit to extend through said sleeve passageway for axially movement with respect thereto;

a locking member mounted near said sleeve proximal end selectively operable in an unlocked state for permitting axial movement of said conduit through said sleeve passageway and in a locked state for preventing axial movement of said conduit through said sleeve passageway; and a protective sheath mounted tightly around said sleeve and covering said layer of porous material for avoiding abrasion damage to adjacent patient tissue when said sleeve distal end is inserted through said patient's skin incision; and wherein said protective sheath comprises a tubular body formed of thin flexible material having a distal end proximate to said layer of porous material and a proximal end including a tab for pulling said body axially in a proximal direction; and wherein said body includes an axially extending score line and a distal end having a lateral dimension less than the lateral dimension of said layer of porous material whereby said sheath body will tear along said score line as said body distal end is pulled axially in a proximal direction by said tab.

2. The assembly of claim 1 further including a sealing device configured to contact said conduit outer surface for preventing migration of deleterious material through said sleeve along said conduit outer surface.

3. The assembly of claim 2 wherein said sealing device comprises a compressible seal and said locking member in said locked state compresses said seal against said conduit outer surface.

4. The assembly of claim 3 wherein said compressible seal comprises a ring extending around said conduit outer surface and wherein said locking member is mounted on said conduit for movement there along to squeeze said seal against said sleeve inner surface and said conduit outer surface.

5. The assembly of claim 4 wherein said sleeve inner surface defines a recess adjacent said sleeve proximal end for accommodating said compressible seal.

6. The assembly of claim 4 further including a latch operable to releasably latch said locking member to said sleeve.

7. The assembly of claim 4 further including an extensible seal member mounted around said conduit and having a distal end secured to said locking member and a proximal end secured to the conduit outer surface.

8. The assembly of claim 1 further including an anchor member mounted near said sleeve proximal end adapted for external attachment to a patient's outer skin surface.

9. The assembly of claim 1 wherein said layer of porous material incorporates antimicrobial and/or anti-inflammatory agents.

10. An apparatus suitable for percutaneous implantation in a patient's body, said apparatus including;

an elongate sleeve having first and second ends, said sleeve comprising a wall having a peripheral outer surface and a peripheral inner surface defining a passageway extending from said first to said second end;

said sleeve outer surface having a substantially uniform diameter dimensioned for insertion through a patient's skin incision for subcutaneous placement of said sleeve second end;

an elongate catheter extending through said passageway and configured for slidable movement with respect thereto;

a layer of porous material mounted on said sleeve outer surface proximate to said sleeve second end, said layer of porous material dimensioned for insertion through said incision for placement in the dermis of a patient's body for promoting tissue ingrowth to form an infection resistant barrier;

an anchor member mounted near said sleeve first end for externally attaching said sleeve to the outer skin surface of said patient;

an annular seal member mounted around said catheter adjacent said sleeve first end;

means for sealing said annular seal member against the outer surface of said catheter for preventing the migration of deleterious material between said sleeve inner surface and said catheter outer surface; and a protective sheath mounted tightly around said sleeve and covering said layer of porous material for avoiding abrasion damage to adjacent patient tissue when said sleeve distal end is inserted through said patient's skin incision; and wherein said protective sheath comprises a tubular body formed of thin flexible material having a distal end proximate to said layer of porous material and a proximal end including a tab for pulling said body axially in a proximal direction; and wherein said body includes an axially extending score line and a distal end having a lateral dimension less than the lateral dimension of said layer of porous material whereby said sheath body will tear along said score line as said body distal end is pulled axially in a proximal direction by said tab.

11. The apparatus of claim 10 wherein said means for sealing includes a compression member for pressing said seal member against said sleeve and said catheter.

12. The apparatus of claim 11 including means for selectively latching said compression member for preventing catheter movement in said passageway and unlatching said compression member to permit catheter movement in said passageway.

13. The apparatus of claim 10 wherein said sleeve defines a recess adjacent to said first end; and wherein said annular seal member is configured to be accommodated in said recess.

14. The apparatus of claim 11 wherein seal member is formed of compressible material; and wherein said means for sealing includes means for compressing said seal member against said sleeve and said catheter.

15. The apparatus of claim 10 further including:

an extensible seal member mounted around said catheter, said seal member having a distal end secured to said sleeve and a proximal end secured to the outer surface of said catheter.

16. The apparatus of claim 10 wherein said layer of porous material incorporates antimicrobial and/or anti-inflammatory agents.

17. A method of forming a percutaneous port through a patient's skin for providing catheter access to interior body sites, said method comprising:

forming an incision extending through a patient's epidermis and dermis layers;

providing an elongate sleeve having a distal end and a proximal end, an outer peripheral surface of substantially uniform diameter dimensioned for insertion through said incision, and an inner peripheral surface defining a passageway extending axially from said distal end to said proximal end;

providing a layer of porous material around said sleeve outer peripheral surface proximate to said sleeve distal end, said layer of porous material dimensioned for insertion through said incision;

providing a tubular sheath having a distal portion and a proximal portion and a preformed score line extending axially therebetween;

mounting said sheath tightly around said sleeve with said sheath distal portion covering said layer of porous material;

providing a catheter having a distal end and a proximal end;

sliding said catheter through said sleeve passageway;

inserting said sleeve distal end and said sheath distal portion through said incision to position said porous material layer adjacent said patient's dermis layer for promoting tissue ingrowth;

pulling said sheath proximal portion axially to tear said sheath along said score line and away from said sleeve and said layer of porous material;

sealing the proximal end of said sleeve to prevent the migration of deleterious material along said catheter outer surface into said body; and anchoring the proximal end of said sleeve to the patient's outer skin surface.

18. The method of claim 17 wherein said step of sealing includes placing an annular seal around said catheter outer surface adjacent to said sleeve proximal end; and pressing said annular seal against said catheter outer surface and said sleeve to prevent the migration of deleterious material therebetween.

19. The method of claim 17 wherein said pressing step includes selectively latching a compression member against said annular seal to lock said catheter in position in said sleeve passageway.

20. The method of claim 17 further including the step of unlatching said compression member to permit said catheter to slide in said sleeve passageway for repositioning and/or replacing said catheter.

* * * * *